United States Patent
Segtnan

(10) Patent No.: US 11,969,240 B2
(45) Date of Patent: Apr. 30, 2024

(54) METHOD OF ESTABLISHING A BRAIN STATUS INDICATION PARAMETER AND SYSTEM THEREFOR

(71) Applicant: Synaptic ApS, Odense C (DK)

(72) Inventor: Eivind Antonsen Segtnan, Odense C (DK)

(73) Assignee: Synaptic ApS, Odense C (DK)

( * ) Notice: Subject to any disclaimer, the term of this patent is extended or adjusted under 35 U.S.C. 154(b) by 200 days.

(21) Appl. No.: 17/289,610

(22) PCT Filed: Oct. 30, 2019

(86) PCT No.: PCT/DK2019/050327
§ 371 (c)(1),
(2) Date: Apr. 28, 2021

(87) PCT Pub. No.: WO2020/088730
PCT Pub. Date: May 7, 2020

(65) Prior Publication Data
US 2021/0393224 A1    Dec. 23, 2021

(30) Foreign Application Priority Data
Oct. 31, 2018 (DK) .......................... PA 2018 70707

(51) Int. Cl.
*A61B 5/00*       (2006.01)
*A61B 5/055*      (2006.01)
(Continued)

(52) U.S. Cl.
CPC ............ *A61B 5/055* (2013.01); *A61B 5/4088* (2013.01); *A61B 5/4866* (2013.01); *A61B 6/037* (2013.01); *A61B 6/501* (2013.01); *G06V 10/267* (2022.01)

(58) Field of Classification Search
CPC ...................................................... A61B 5/055
See application file for complete search history.

(56) References Cited

U.S. PATENT DOCUMENTS

2005/0215889 A1    9/2005   Patterson, II
2007/0160277 A1    7/2007   Slabaugh et al.
(Continued)

FOREIGN PATENT DOCUMENTS

JP       2011000439 A      1/2011
WO   WO2007/018755 A1    2/2007
(Continued)

OTHER PUBLICATIONS

Segtnan et al. ("Prognostic Implications of Total Hemispheric Glucose Metabolism Ratio in Cerebrocerebellar Diaschisis" JNucl Med. vol. 58, No. 5, Published online Oct. 27, 2016 (Year: 2016).*
(Continued)

*Primary Examiner* — Joseph M Santos Rodriguez
(74) *Attorney, Agent, or Firm* — Lee & Hayes, P.C.

(57) ABSTRACT

A method of establishing a brain status indication parameter indicative of a brain disorder is disclosed. The method comprising the steps: —determining a brain energy metabolism indicator of at least a part of the brain of a subject, —determining a skull energy metabolism indicator of at least a part of the skull of said subject, —establishing the brain status indication parameter by at least relating said brain energy metabolism indicator to said skull energy metabolism indicator. Also disclosed are a system for establishing such brain status indication parameter, a computer program, and methods for treating a disease.

17 Claims, 6 Drawing Sheets

(51) Int. Cl.
  *A61B 6/03*    (2006.01)
  *A61B 6/50*    (2024.01)
  *G06V 10/26*   (2022.01)

(56) References Cited

U.S. PATENT DOCUMENTS

2010/0322488 A1   12/2010   Virtue et al.
2011/0105881 A1    5/2011   Kakimoto et al.

FOREIGN PATENT DOCUMENTS

WO   WO2008/107809 A2   9/2008
WO   WO2018/152339 A1   8/2018

OTHER PUBLICATIONS

Zhu et al. "Quantitative imaging of brain energy metabolism and neroenergetics using in vivo X-nuclear 2H, 17O and 31P MRS and ultrahigh field" J Magn Reson 292, p. 155-170, Jul. 2018 (Year: 2018).*

International Search Report and Written Opinion dated Dec. 11, 2019 in International application No. PCT/DK2019/050327, 10 pages.

Chetouani et al., "Cross-Section Variation of White and Grey Matter in Older Hypertensive Patients with Subjective Memory Complaints," Jan. 2018, NeuroImage: Clinical, 17:804-810.

Haxby et al., "Relations Between Neuropsychological and Cerebral Metabolic Asymmetries in Early Alzheimer's Disease," Jun. 1985, Journal of Cerebral Blood Flow and Metabolism, 5(2):193-200.

Danish Search Report dated Aug. 28, 2019 in Danish Application No. PA 2018 70707, 4 pages.

Japanese Office Action dated Jun. 6, 2023 for Japanese Patent Application No. 2021-547641, a foreign counterpart to U.S. Appl. No. 17/289,610, 8 pages.

* cited by examiner

100
METHOD OF ESTABLISHING A BRAIN STATUS INDICATION PARAMETER AND SYSTEM THEREFOR

CROSS REFERENCE TO RELATED APPLICATIONS

This Application is a U.S. National Phase Application of International Application No. PCT/DK2019/050327, filed Oct. 30, 2019, which claims priority to Danish Patent Application No. PA 2018 70707, filed Oct. 31, 2018, which are incorporated herein by reference in their entirety.

FIELD OF INVENTION

The invention relates to a method for establishing a brain status indication parameter, particularly a brain status indication parameter indicative of brain disorders relating to diaschisis. The invention further relates to a system for establishing such brain status indication parameter, a computer program, and methods for treating a disease.

BACKGROUND OF THE INVENTION

The use of imaging techniques as input for diagnosing brain disorders has become extremely common. Nevertheless, such images are typically evaluated with respect to a specific area of the brain which is suspected to be affected. Also, the evaluation leading to the diagnosis may typically be done by the medical practitioner, leading to an inherently subjective nature of the findings which forms the basis for making the diagnosis.

Thus, it continues to be a challenge to arrive at more accurate diagnoses.

An object of the present invention is to solve the above challenges.

SUMMARY

The invention relates to a method of establishing a brain status indication parameter indicative of a brain disorder, the method comprising the steps:
- determining a brain energy metabolism indicator of at least a part of the brain of a subject,
- determining a skull energy metabolism indicator of at least a part of the skull of said subject,
- establishing the brain status indication parameter by at least relating said brain energy metabolism indicator to said skull energy metabolism indicator.

One advantage of the invention is that a likelihood of presence of a brain disorder may be established with a higher accuracy than previously known methods. By relating the brain energy metabolism indicator with the skull energy metabolism indicator, an indication of the status of the brain is obtained as the brain status indication parameter. The brain status indication parameter may therefore be a highly valuable input for a medical practitioner in the process of diagnosing a subject.

Particularly, by including the relation between the skull energy metabolism indicator and the brain energy metabolism indicator, variations between different subjects with respect to the energy metabolism in the brain can be at least partly accounted for to obtain a more accurate brain status indication parameter.

Surprisingly, the present inventor discovered that by relating said brain energy metabolism indicator to said skull energy metabolism indicator an unprecedented accuracy with respect to the brain status indication parameter, even across different types of etiology in brain disorders. In advantageous embodiments the relation between said brain energy metabolism indicator and said skull energy metabolism is a ratio.

A significant advantage of the invention is that deviations from subject to subject are countered by using the relation between the brain energy metabolism indicator and the skull energy metabolism indicator. In other words, using the mentioned relation helps to make the values comparable in the sense that deviation from normal values can be detected. Previous measurements for the same subject could in theory be comparable, but can in practice not be relied upon, since such only exists for exceptionally few subjects, and further since even minor changes in equipment and their settings may lead to different absolute values, and thus remove the comparability. The present inventor discovered that by using the skull values of the same subject a suitable reference value was obtained, i.e. by comparing the energy metabolism value of the brain or part thereof to the energy metabolism value of the skull or part thereof, the variations between subjects could be at least partly accounted for.

Even in cases when images of the brain do not provide any conclusive input to the medical practitioner, the brain status indication parameter of the present invention may still provide an indication of presence of a brain disorder, possibly even an indication specific type of brain disorder.

Advantageously, by providing the medical practitioner with a parameter of diagnostic relevance in the form of the brain status indication parameter, a more accurate and fast diagnosis is facilitated, which again facilitates a more accurate and fast treatment. Therefore, a significant advantage of the present invention may be that it facilitates increased chance of successful treatment, including higher chance of survival, more effective mitigation of adverse effects of the disease or condition, mitigated side effects etc.

In the present context, the term "brain" refers to the whole brain, i.e. including the cerebrum and the cerebellum, unless otherwise specifically stated.

In the present context the term "brain energy metabolism indicator" refers to an indicator of the brain energy metabolism. It is noted that "energy metabolism" and "glucose metabolism" is used interchangeably herein. Particularly, it is noted that the brain energy metabolism indicator is related to at least a part of the brain. Thus, the brain energy metabolism indicator may be determined on the basis of a part of the brain in some embodiments, and on the basis of the whole brain in some other embodiments. Examples of parts of the brain for this purpose include the cerebrum, or part thereof such as the left or right hemisphere of the cerebrum, or another part of the cerebrum, the cerebellum, or part thereof such as the left or right hemisphere of the cerebellum, or another part of the cerebellum, the left or right hemisphere of the whole brain, or another part of the brain. It is also noted that the brain energy metabolism indicator includes both direct indicators, such as FDG-PET, and more indirect indicators showing e.g. neural activity or blood flow, which is associated with energy metabolism. The cerebellum comprises two hemispheres, a right hemisphere and a left hemisphere. Similarly, the cerebrum comprises two hemispheres, a right hemisphere and a left hemisphere. When referring to e.g. the left hemisphere of the brain, the left hemisphere of the cerebrum and of the cerebellum is meant, unless otherwise specifically stated. According to the invention, establishing the brain status indication parameter includes at least relating said brain energy metabolism indicator to said skull energy metabolism indicator. In some embodiments, further parameters and/or calculations are done to obtain the brain status indication parameter.

In the present context the term "skull energy metabolism indicator" refers to an indicator of the skull energy metabolism. It is noted that "energy metabolism" and "glucose metabolism" is used interchangeably herein. Particularly, it is noted that the skull energy metabolism indicator is related to at least a part of the skull. Thus, the skull energy metabolism indicator may be determined on the basis of a part of the skull in some embodiments, and on the basis of the whole skull in some other embodiments. It is also noted that the skull energy metabolism indicator includes both direct indicators, such as FDG-PET, and more indirect indicators showing e.g. blood flow, which is associated with energy metabolism.

In the context of the present invention, the term "brain disorder indication parameter" is used as a parameter indicating the status of the brain and may indicate the likelihood of existence of a brain disorder and/or the type(s) of brain disorder(s) for the subject in question. In some embodiments, especially in simpler implementations, the brain disorder indication parameter is a number or value, typically between two predefined end point values. In some embodiments, especially in more refined implementations, the brain disorder indication parameter may comprise a set of numbers or values, each of which may indicate e.g. a likelihood of a certain type of brain disorder. In some embodiments, the brain disorder indication parameter does not include a likelihood of a certain type of brain disorder. It is noted that brain disorder indication parameter serves as an intermediate finding of diagnostic relevance in the sense that it does not replace a diagnosis but can be used as input by a medical practitioner in order to arrive at such diagnosis. Thus, the medical practitioner would include further steps, such as attributing the values of the brain disorder indication parameter to a certain clinical picture. In some embodiments, this would require input of further parameters of diagnostic relevance.

In the present context the term "relating" may refer to various forms of correlating or comparing, i.e. a relation between said brain energy metabolism indicator to said skull energy metabolism indicator. In advantageous embodiments, the relating comprises at least finding the ratio between the two.

In the present context the term "brain disorder" is understood to broadly cover abnormalities related to the brain. It is noted that it may cover both causes (e.g. brain cancer) and resulting conditions (diaschisis). Thus, the various brain disorders mentioned herein may in some cases be somewhat overlapping. Examples of brain disorders include Alzheimer's disease, Parkinson's disease, mild cognitive impairment (MCI), glioma, traumatic brain injury, apoplexy, neurosurgery (i.e. effects thereof) and probable drug side effects to the brain parenchyma.

In the present context, the term "brain status establishment system" is understood as a system adapted to record measurements from subjects and establish a brain status indication parameter for each subject. In some embodiments, the system may further be configured to arrive at a diagnosis using at least the brain status indication parameter in the sense that a recommended treatment can readily be applied.

According to an advantageous embodiment of the invention said relating involves calculating a ratio between the brain energy metabolism indicator and the skull energy metabolism indicator, or vice versa.

An advantage of the above embodiment may be that variations between different subjects with respect to the energy metabolism in the brain can be at least partly accounted for to obtain more accurate brain status indication parameter. Particularly, by using the ratio between the brain energy metabolism indicator and the skull energy metabolism indicator (or vice versa) a more accurate measure with respect to brain disorder may be obtained, which is much less vulnerable for variations between subjects. This in turn supports the decision making of the medical practitioner to arrive at correct diagnosis and treatment adapted and tailored for the specific subject.

According to an alternative embodiment, the relating may be in the form:

$$\text{Skull-brain ratio} = Sk_i^a Br_j^b$$

Here, i denotes the i'th part of the skull, j denotes the j'th part of the brain, a and b denote exponents, where a and b have opposite signs, i.e. a is positive and b is negative or vice versa.

It is noted that this embodiment includes the ratio between the two values when a and b are unity values of opposite signs.

According to an alternative embodiment, the relating may be in the form:

$$\text{Skull-brain ratio} = k_0(Sk_i+k_1)^a(Br_j+k_2)^b$$

Here, i denotes the i'th part of the skull, j denotes the j'th part of the brain, a and b denote exponents, where a and b have opposite signs, i.e. a is positive and b is negative or vice versa. Further, $k_0$, $k_1$ and $k_2$ are constant values.

It is noted that when $k_1=k_2=0$, the relation reduces to the above described relation.

According to an advantageous embodiment of the invention said relating comprises calculating a ratio between the brain energy metabolism indicator and the skull energy metabolism indicator.

According to an advantageous embodiment of the invention said part of the brain comprises at least the left hemisphere of cerebellum.

Using the left hemisphere of the cerebellum in determining of the brain energy metabolism indicator, or when determining at one or more further brain energy metabolism indicators in determining of the brain energy metabolism indicator and/or at least one of the one or more further brain energy metabolism indicators.

According to an advantageous embodiment of the invention said part of the brain comprises at least the right hemisphere of cerebellum.

According to an advantageous embodiment of the invention said part of the brain comprises at least the left hemisphere of cerebrum.

According to an advantageous embodiment of the invention said part of the brain comprises at least the right hemisphere of cerebrum.

According to an advantageous embodiment of the invention the brain energy metabolism indicator of the brain of the subject is determined.

Thus, in the above embodiment of the brain energy metabolism indicator the whole brain is determined. In other words, the step of determining brain energy metabolism indicator of at least a part of the brain of said subject consists of determining brain energy metabolism indicator of the whole brain of said subject.

According to an advantageous embodiment of the invention the part of the brain comprises at least the 50 percent most active nerve fibers.

According to an advantageous embodiment of the invention the method comprises establishing a degree of symmetry between at least a part of the right hemisphere of the brain and a corresponding part of the left hemisphere of the brain.

An advantage of the above embodiment may be that a very high accuracy brain status indication parameter may be obtained.

It is noted that a healthy brain normally exhibits a high degree of symmetry and that deviating from such high degree of symmetry indicates presence of a brain disorder.

According to an advantageous embodiment of the invention the degree of symmetry comprises a ratio between at least a part of the right hemisphere of the brain and a corresponding part of the left hemisphere of the brain.

According to an advantageous embodiment of the invention the degree of symmetry comprises a ratio between the right hemisphere of the cerebrum and the left hemisphere of the cerebrum.

According to an advantageous embodiment of the invention the degree of symmetry comprises a ratio between the right hemisphere of the cerebellum and the left hemisphere of the cerebellum.

According to an advantageous embodiment of the invention the degree of symmetry comprises a ratio between the right hemisphere of the cerebrum and the left hemisphere of the cerebrum, and a ratio between the right hemisphere of the cerebellum and the left hemisphere of the cerebellum.

According to an advantageous embodiment of the invention the degree of symmetry comprises a ratio between the right hemisphere of the brain and the left hemisphere of the brain.

According to an advantageous embodiment of the invention said brain energy metabolism indicator is determined from a brain energy metabolism indicator distribution.

According to an advantageous embodiment of the invention said skull energy metabolism indicator is determined from a skull energy metabolism indicator distribution.

In an embodiment the brain energy metabolism indicator is determined from a brain energy metabolism indicator distribution and the skull energy metabolism indicator is determined from a skull energy metabolism indicator distribution indicator.

According to an advantageous embodiment of the invention a segmentation on the brain energy metabolism indicator distribution is performed to obtain a brain energy metabolism indicator in one or more parts of the brain.

According to an advantageous embodiment of the invention the method comprises a correction ratio for segmentation errors by relating at least one hemisphere of the skull to the contralateral hemisphere of the skull.

According to an advantageous embodiment of the invention said correction for segmentation errors comprises a ratio between the right hemisphere of the skull and the left hemisphere of the skull.

According to an advantageous embodiment of the invention the method further comprises the step of determining one or more further brain energy metabolism indicators of at least a part of the brain of the subject.

As an example, said brain energy metabolism indicator and said one or more further brain energy metabolism indicators may be obtained from segmentation of a brain energy metabolism indicator distribution, e.g. in the form of one or more brain energy metabolism indicator images.

According to an advantageous embodiment of the invention the method further comprises the step of determining one or more further skull energy metabolism indicators of at least a part of the skull of the subject.

As an example, said skull energy metabolism indicator and said one or more further skull energy metabolism indicators may be obtained from segmentation of a skull energy metabolism indicator distribution, e.g. in the form of one or more skull energy metabolism indicator images.

In an advantageous embodiment of the invention, the method further comprises a segmentation comprising dividing the brain energy metabolism indicator distribution into a number of substantially regularly shaped three-dimensional zones.

In an embodiment of the invention, the method comprises a segmentation of the brain or a part thereof, the segmentation comprising dividing the brain energy metabolism indicator distribution into a number of substantially regularly shaped three-dimensional zones.

In an advantageous embodiment of the invention, each of the zones corresponds to at least one voxel of the brain energy metabolism indicator distribution.

In an advantageous embodiment of the invention, the method further comprises establishing a synaptic entropy network indication parameter by at least relating said synaptic entropy indicator to a corresponding normalized synaptic entropy indicator being a synaptic entropy indicator of a normal population.

In the present context, the term "synaptic entropy indicator" refers to an indicator of the brain entropy. The synaptic entropy indicator may e.g. be determined on the basis of at least one voxel in some embodiments, and on the basis of a plurality of voxels in the whole brain in some other embodiments.

By relating the synaptic entropy indicator with the normalized synaptic entropy indicator, an indication of the status of disorderliness of the synaptic network may be obtained as the synaptic entropy network indication parameter. A normalized synaptic entropy indicator may be obtained from e.g. at least 30 healthy subjects, such as at least 100 healthy subjects.

In the above embodiment, the synaptic entropy indicator is of course related to the corresponding normalized synaptic entropy indicator, i.e. the normalized synaptic entropy indicator corresponding to the same part(s) of the brain as the synaptic entropy indicator.

As an example, the brain may be divided into a number of planes, e.g. horizontal planes (i.e. "slices"), where the synaptic entropy network indication parameter $H_S$ for each plane is calculated as $$H_S = -\sum_{\substack{1 \le i \le m \\ 1 \le j \le n}} P_{i,j} \log_b P_{i,j}$$

where i and j represent the location of each pixel, m is the number of rows, n is the number of columns, and b is the base of logarithm (let it be 2 for binary logarithm). The synaptic entropy network indication parameter of the entire brain $H_T$ is then calculated as $$H_T = \Sigma H_S$$

In a sense, the synaptic entropy network indication parameter as calculated above for each plane and the entire brain may be view as a measure of the entropy for each plane and the entire brain, respectively.

In an embodiment of the invention, each voxel corresponds to a single value of the brain energy metabolism indicator distribution, i.e. the smallest unit of an image obtained by the applied neuroimaging technique.

In an embodiment of the invention, each voxel corresponds to a summation of a number of values of the brain energy metabolism indicator distribution. This may especially be advantageous to reduce the subsequent data processing of the voxels, by reducing the number of voxels.

In an embodiment of the invention, the brain energy metabolism indicator distribution is divided in at least 5 zones for each dimension. Thus, in this embodiment the brain energy metabolism indicator distribution would have at least 125 voxels.

In an embodiment of the invention, the brain energy metabolism indicator distribution is divided in at least 10 zones for each dimension. Thus, in this embodiment the brain energy metabolism indicator distribution would have at least 1000 voxels.

In an advantageous embodiment of the invention, establishing the brain status indication parameter further comprises integrating the relation between said brain energy metabolism indicator and said skull energy metabolism indicator with said synaptic entropy network indication parameter.

According to an advantageous embodiment of the invention the method comprises a further step of relating said brain energy metabolism indicator or one of said further brain energy metabolism indicators to said skull energy metabolism indicator or one of said further skull energy metabolism indicators,
wherein at least one of said further brain energy metabolism indicators or one of said further skull energy metabolism indicators is used.

For example, one or more brain energy metabolism indicator(s) related to the cerebrum or part thereof and/or one or more brain energy metabolism indicator(s) related to the cerebellum or part thereof may be used.

According to an advantageous embodiment of the invention the energy metabolism indicator is determined by a neuroimaging technique, such as a functional Magnetic Resonance Imaging (fMRI) based technique, a Computed Tomography (CT) Scan based technique, a Positron Emission Tomography (PET) based technique, a Magnetoencephalography (MEG) or Electroencephalography (EEG) based technique, a Single-Photon Emission Computed Tomography (SPECT) based technique, or an ultrasound (US) based technique.

The above techniques are suitable for use in establishing the energy metabolism indicator, e.g. via an energy metabolism indicator distribution. An advantage of using an energy metabolism indicator distribution technique is that segmentation of the brain into subparts may be relatively easy.

According to an embodiment of the invention the energy metabolism indicator is determined by a neuroimaging technique, such as a functional Magnetic Resonance Imaging (fMRI) based technique, a Computed Tomography (CT) Scan based technique, a Positron Emission Tomography (PET) based technique, a Single-Photon Emission Computed Tomography (SPECT) based technique.

According to an advantageous embodiment of the invention the energy metabolism indicator is determined by a Positron Emission Tomography (PET) based technique.

An advantage of the above embodiment may be that a relatively direct indication of the energy metabolism may be obtained, e.g. by using a Positron Emission Tomography (PET) based technique with a tracer, such as fludeoxyglucose (FDG).

According to an advantageous embodiment of the invention the energy metabolism indicator is determined by a magnetic resonance imaging (MRI) based technique, such as a functional Magnetic Resonance Imaging (fMRI) based technique.

An advantage of the above embodiment may be that the energy metabolism may be determined from the indication provided by the MRI-based technique, such as fMRI-based technique.

According to an advantageous embodiment of the invention a tracer, such as a radioactive tracer, is used in determination of the energy metabolism indicator.

According to an advantageous embodiment of the invention the energy metabolism indicator is determined by a Positron Emission Tomography (PET) based technique with fludeoxyglucose (FDG) as a tracer.

According to an advantageous embodiment of the invention the brain status indication parameter gives an indication of a presence of the brain disorder or not.

According to an advantageous embodiment of the invention the brain status indication parameter gives an indication of a probability of presence of the brain disorder.

According to an advantageous embodiment of the invention the brain status indication parameter gives an indication of a type of the brain disorder.

According to an advantageous embodiment of the invention the brain disorder is selected from diaschisis; brain tumor, such as Glioma; Mild Cognitive Impairment (MCI); and Alzheimer's disease (AD).

According to an advantageous embodiment of the invention the brain disorder comprises diaschisis.

An advantage of the above embodiment may be that diaschisis may be correlate with several other brain disorders, such as e.g. glioma and Alzheimer's disease. The diaschisis may in an embodiment include the so-called "network diaschisis", which crosses the boundaries of the resting state networks.

Diaschisis is a phenomenon expressed in the neurological and biological network of the brain. Diaschisis may for example be activated in cerebrum and disseminate to cerebellum, and/or vice versa. As yet, in more than a number of different physiological alterations of the brain, it could be expressed by definition that diaschisis exists in the whole network of the brain, i.e. as network diaschisis. E.g., it may be developed both in the neuronal connection of the connectome, and also by and from the biological cells of glia in the brain parenchyma. Thus, diaschisis can be defined as the energetic transposition that transposes both in, and between synapses of the brain altering the order, say entropy, among synapses. The energetic transposition causes the synaptic network to function in a unity. For the emphasis on the unity of the synaptic network, this may also be referred to as synapsome that encompasses the whole brain in one single entity, where synapsome refers to "synapse", the junction between nerve cells, and "ome", referring to all constituents being considered collectively, i.e. emphasizing the network aspect.

The present invention may provide a very accurate brain status indication parameter with respect to diaschisis.

According to an advantageous embodiment of the invention the brain comprises brain tumor, such as Glioma.

According to an advantageous embodiment of the invention the brain disorder comprises Mild Cognitive Impairment (MCI).

According to an advantageous embodiment of the invention the brain disorder comprises Alzheimer's disease (AD).

According to an embodiment of the invention, the brain status indication parameter indicative comprises an expression of cerebral function. The cerebral function may appear that a ratio of the energy metabolism indicator of the cerebrum to the whole brain.

According to an embodiment of the invention, the brain status indication parameter indicative comprises an expression of cerebral function, and the relation between said brain energy metabolism indicator to said skull energy metabolism indicator.

According to an embodiment of the invention, the brain status indication parameter indicative comprises an expression of the degree of symmetry between at least a part of the right hemisphere of the brain and a corresponding part of the left hemisphere of the brain, and the relation between said brain energy metabolism indicator to said skull energy metabolism indicator.

According to an embodiment of the invention, the brain status indication parameter indicative comprises an expression of cerebral function, an expression of the degree of symmetry between at least a part of the right hemisphere of the brain, and the relation between said brain energy metabolism indicator to said skull energy metabolism indicator.

According to an advantageous embodiment of the invention the step of establishing the brain status indication parameter is carried out by a computer.

The invention further relates to a brain status establishment system for establishing a brain status indication parameter indicative of a brain disorder, the system comprising:
a brain scanning device configured to
determine a brain energy metabolism indicator of at least a part of the brain of a subject,
determine a skull energy metabolism indicator of at least a part of the skull of said subject,
a computer device configured to establishing the brain status indication parameter by at least relating said brain energy metabolism indicator to said skull energy metabolism indicator.

According to an embodiment of the invention, the brain status establishment system according to the invention or any of its embodiments is configured to operate in accordance with the method of establishing a brain status indication parameter according to the invention or any of its embodiments.

The brain scanning device may a neuroimaging scanner, such as a functional Magnetic Resonance Imaging (fMRI) scanner, a Computed Tomography (CT) scanner, a Positron Emission Tomography (PET) scanner, a Magnetoencephalography (MEG) or Electroencephalography (EEG) scanner, a Single-Photon Emission Computed Tomography (SPECT) scanner, or an ultrasound (US) scanner, or any other scanner capable of measuring energy metabolism or an indicator thereof in the brain and skull.

The invention further relates to a computer program comprising instructions which, when the program is executed by a computer, cause the computer to carry out the steps of the method of any of the preceding claims.

The invention further relates to a method of treating a disease comprising performing the method according to any of the preceding claims before administering a drug or performing surgery.

The invention further relates to a method of treating a disease comprising performing the method according to any of the preceding claims before performing physical exercise.

FIGURES

The invention will now be described with reference to the figures where
FIG. 1A illustrates a method of establishing a brain status indication parameter according to an embodiment of the invention,
FIG. 1B illustrates a method of establishing a brain status indication parameter according to an embodiment of the invention,
FIG. 2 illustrates a brain status establishment system according to an embodiment of the invention,
FIG. 3 illustrates a segmentation step according to an embodiment of the invention,
FIGS. 4A-4B illustrate a trans-axial view of an energy metabolism indicator distribution image according to an embodiment of the invention,
FIGS. 5A-5B illustrate a trans axial view of an energy metabolism indicator distribution image according to an embodiment of the invention,
FIG. 6A illustrates a coronal view of an energy metabolism indicator distribution image according to an embodiment of the invention, and
FIG. 6B illustrates a sagittal view of an energy metabolism indicator distribution image according to an embodiment of the invention.

DETAILED DESCRIPTION

Referring to FIG. 1A, a method of establishing a brain status indication parameter BSI according to an embodiment of the invention is described.

The brain status indication parameter BSI provides an indicative of a brain disorder, for example as a likelihood of a brain disorder being present, or as a likelihood of at least one or a group of brain disorders being present, or as a likelihood of one or more specific brain disorders being present.

First, a brain energy metabolism indicator BEM of at least a part of the brain BR of a subject is determined DBI. This may be done by a variety of different techniques, which may provide a more or less direct indication of the energy metabolism.

Then, a skull energy metabolism indicator SEM of at least a part of the skull SK of a subject is determined DSI. This may typically be done by a similar technique as for the brain energy metabolism indicator BEM. In embodiments, the steps of determining a brain energy metabolism indicator BEM and establishing the brain status indication parameter BSI are executed as a single step in the sense that the brain energy metabolism indicator and the skull energy metabolism indicator are obtained from the same image(s) and subsequently segmented into the brain energy metabolism indicator of at least a part of the brain and the skull energy metabolism indicator of at least a part of the skull. This is illustrated in more detail in FIG. 1B and FIG. 3.

Then, the brain status indication parameter BSI established. This involves at least relating said brain energy metabolism indicator to said skull energy metabolism indicator. This relation may comprise e.g. comparing or forming a ratio between the brain energy metabolism indicator and the skull energy metabolism indicator. When using the ratio, this may be the ratio between the brain energy metabolism indicator and the skull energy metabolism indicator, or vice versa.

In some embodiments, this ratio forms part of a single number, or a set of numbers, for example in the sense that it is a factor and/or term in an equation forming basis for calculating the number(s).

Turning to FIG. 1B, a method of establishing a brain status indication parameter BSI according to an embodiment of the invention is described.

First, in a measuring step MES, one or more images of an energy metabolism indicator is recorded. The one or more images are then segmented in a segmentation step SEG. First, the brain part(s) of the image(s) are separated to form basis for determining DBI the brain energy metabolism indicator BEM. Then, the skull part(s) of the image(s) are separated to form basis for determining DSI the skull energy metabolism indicator SEM.

It is noted that the segmentation step SEG may divide the brain into smaller segments, e.g. right and left hemisphere, cerebrum and cerebellum, or right and left hemispheres of both the cerebrum and cerebellum. Smaller segments may also be applied.

In FIG. 1B, the brain energy metabolism indicator determining step DBI is shown before the skull energy metabolism indicator determining step DSI. However, in other embodiments, they may e.g. be performed in the opposite order, partly overlapping or concurrently executed.

Then, a step of demining further parameter(s) DFP is executed according to FIG. 1B. In this step, one or more further parameters may be determined, e.g. from one or more distributions of energy metabolisms of the brain and/or skull forming basis for the brain energy metabolism indicator determination step DBI and/or the skull energy metabolism indicator determination step DSI. These one or more further parameter(s) may include parameters indicative of symmetry aspects of the brain or part thereof, of the cerebral function etc. In some embodiments, this step may be omitted.

Then, a diagnosis establishing step EDI follows. This step comprises at least relating said brain energy metabolism indicator BEM to said skull energy metabolism indicator SEM.

In embodiments comprising a step of demining further parameter(s) DFP, the diagnosis establishing step EDI may further comprise calculations based also on such one or more further parameter(s).

When the method also is directed to treatment of any brain disorder(s) resulting from the diagnosis establishing step EDI, the method comprises a treatment step TRT.

This step may comprise administration of an effective amount of one or more active pharmaceutical ingredients (i.e. one or more drugs) and/or performing surgery.

In some embodiments, the treatment step TRT may comprise performing physical exercises.

Turning to FIG. 2, a brain status establishment system BSS for establishing a brain status indication parameter BSI indicative of a brain disorder. The system (BSS) comprises a brain scanning device BSD and a computer device CD.

The brain scanning device BSD is configured to determine a brain energy metabolism indicator BEM of at least a part of the brain BR of a subject SUB, and to determine a skull energy metabolism indicator SEM of at least a part of the skull (SK) of said subject SUB. In FIG. 2, the brain scanning device BSD is illustrated as a positron emission tomography (PET) scanner but may be any other scanner capable of measuring energy metabolism or an indicator thereof in the brain and skull.

The computer device CD is configured to establish the brain status indication parameter BSI by at least relating said brain energy metabolism indicator BEM to said skull energy metabolism indicator SEM. When further parameter(s) are determined, as described in relation to FIG. 1B, such further parameter(s) may form part of the basis for the establishing of the brain status indication parameter BSI by the computer device CD.

Referring now to FIG. 3, the segmentation step SEG is illustrated according to an embodiment of the invention. First, one or more image(s) of an energy metabolism indicator is recorded, as e.g. illustrated in FIG. 2. As can be seen, the image(s), shown to the upper left, covers both the brain and the skull. Then, the image(s) is segmented, i.e. broken down into at least a skull part and a brain part. In FIG. 3, the brain part is further segmented into a left hemisphere of cerebrum LCE, a right hemisphere of cerebrum RCE, a left hemisphere of cerebellum LCB, and a right hemisphere of cerebellum RCB.

In some further embodiments, the brain and/or the skull is further segmented, e.g. into rather small parts, such as a plurality of square fields. By utilizing computerized segmentation, such fields may be rather small, e.g. giving a resolution of tens or hundreds of fields for each direction in the image. It is noted that such deep segmentation is especially advantageous when advanced computerized processing is available, e.g. using machine learning-based methods, such as deep learning-based methods.

Referring now to FIGS. 4A-4B, 5A-5B, and 6A-6B, an energy metabolism indicator distribution image is illustrated according to an embodiment of the invention. The images shown in FIGS. 4A-4B, 5A-5B, and 6A-6B, is recorded by a Positron Emission Tomography (PET) based technique with fludeoxyglucose (FDG) as a tracer. It is noted that other energy metabolism indicator recording techniques are also usable within the scope of the invention. FIGS. 4A-B, 5A-B, and 6A-B are images of the same subject having been diagnosed with brain cancer. The location of the brain tumor is more easily seen in FIG. 4A, in the upper center part of the image, corresponding to a location in the left part of the cerebrum.

FIGS. 4A and 4B show areas segmented in the cerebrum and the skull, respectively, where the energy metabolism indicator distribution exceeds a certain threshold. FIGS. 4A and 4B are identical, except that FIG. 4B shows segmentation only for the left hemisphere whereas FIG. 4A shows this for both left and right hemispheres. Also, as it can be seen from FIG. 4A in particular, the corresponding emphasized areas are partitioned into left and right hemispheres, both for the skull and the cerebrum.

Figure 1A:
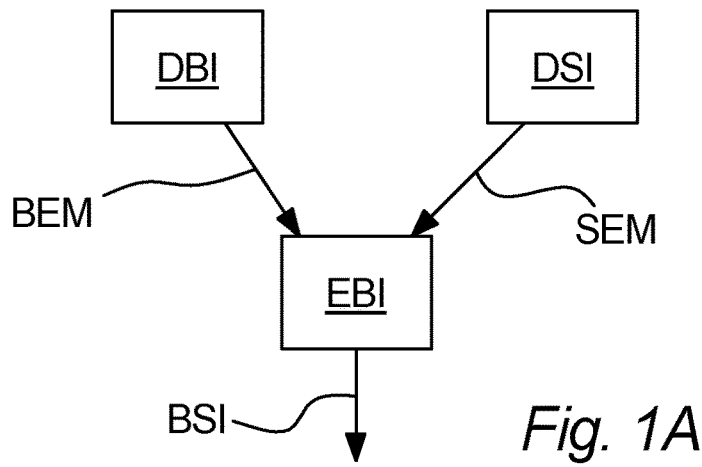
Figure 1B:
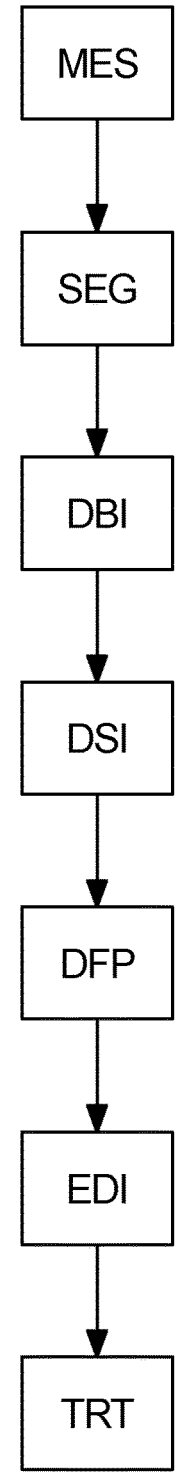
Figure 2:
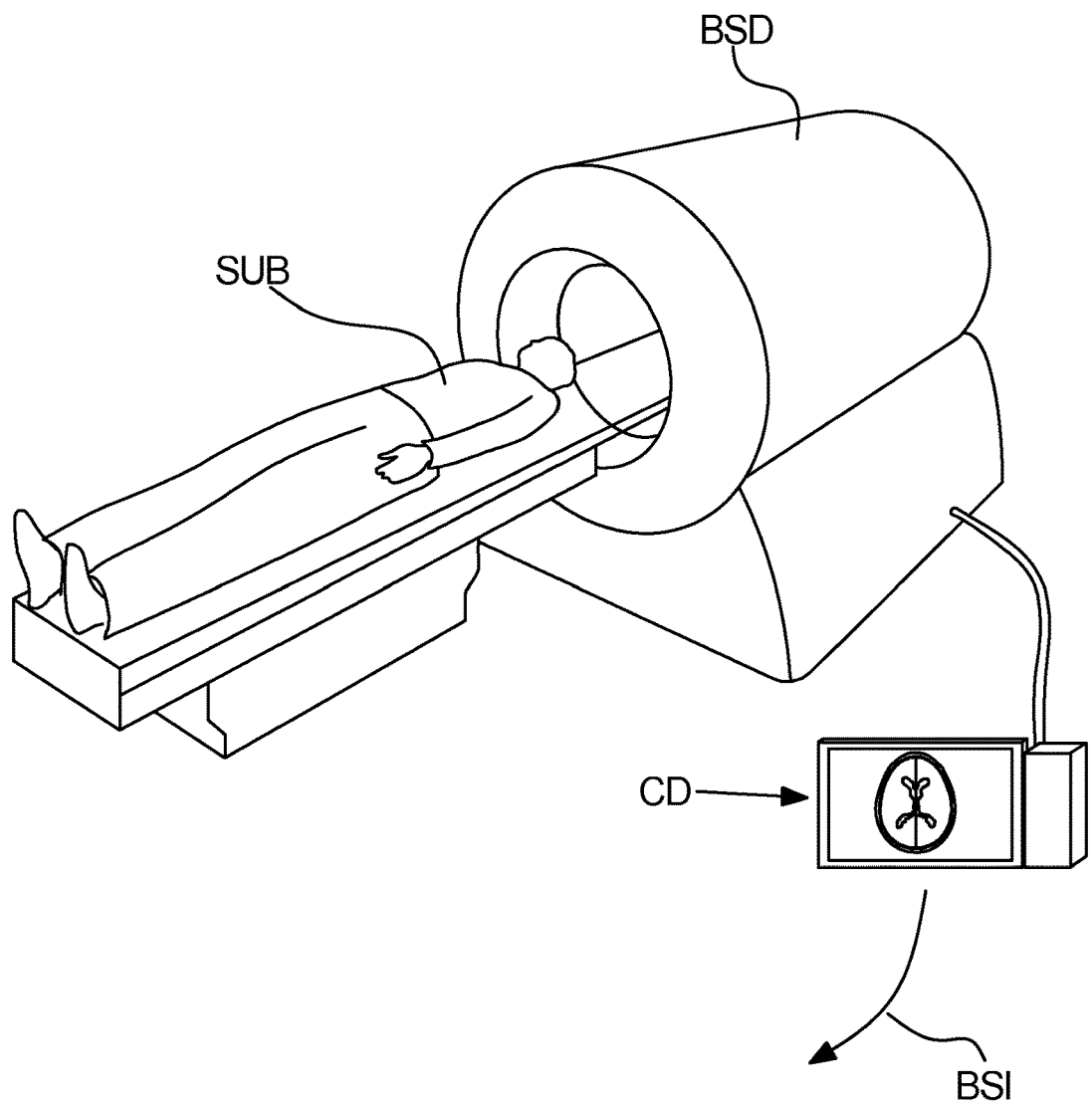
Figure 3:
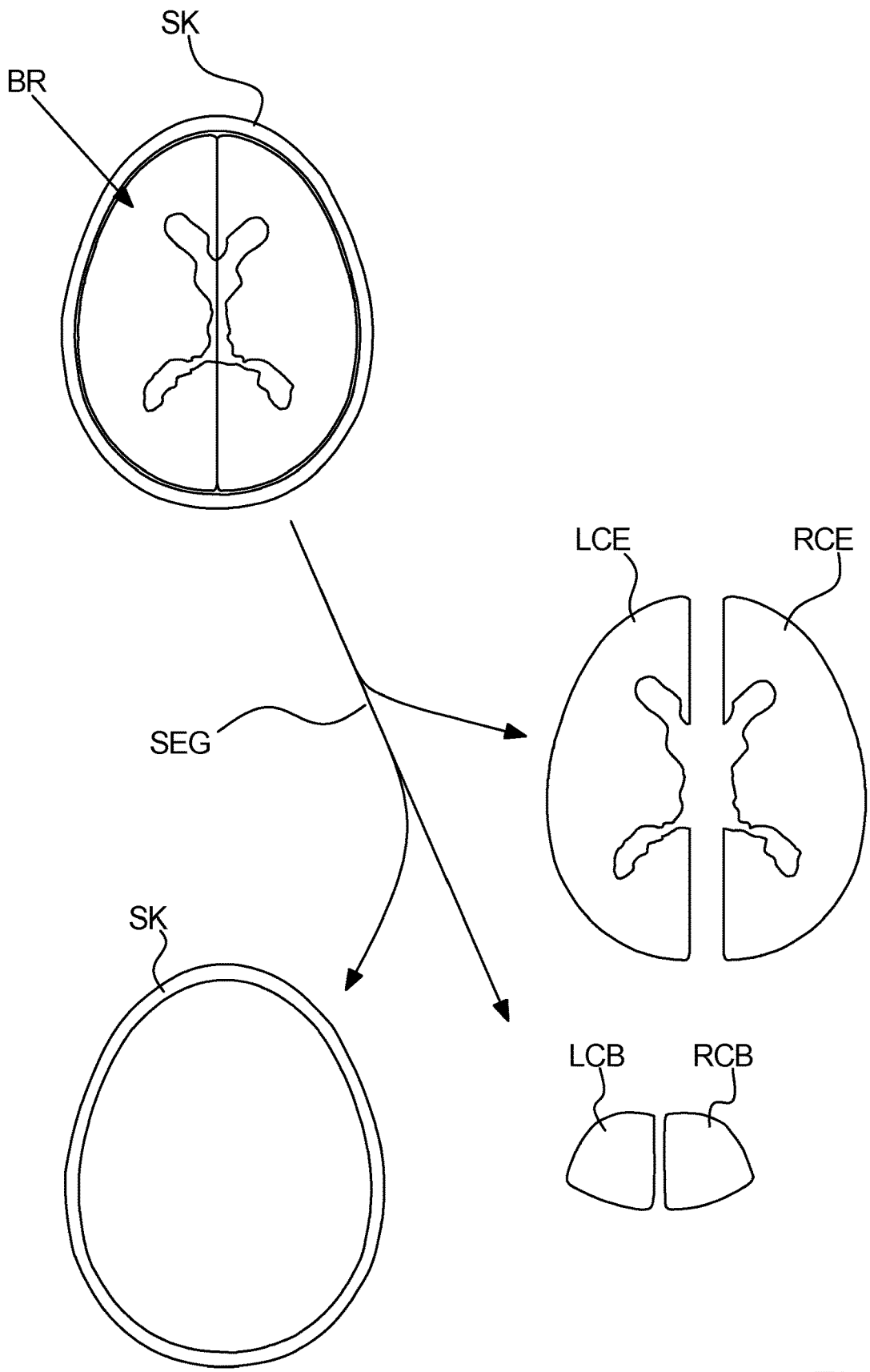
Figure 4A:
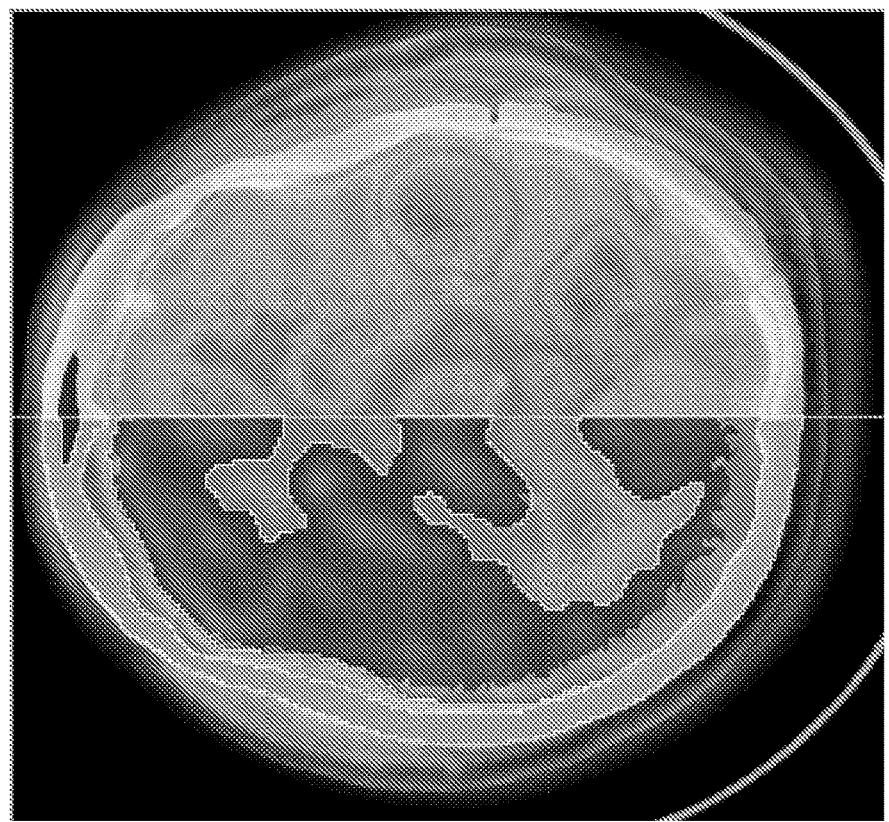
Figure 4B:
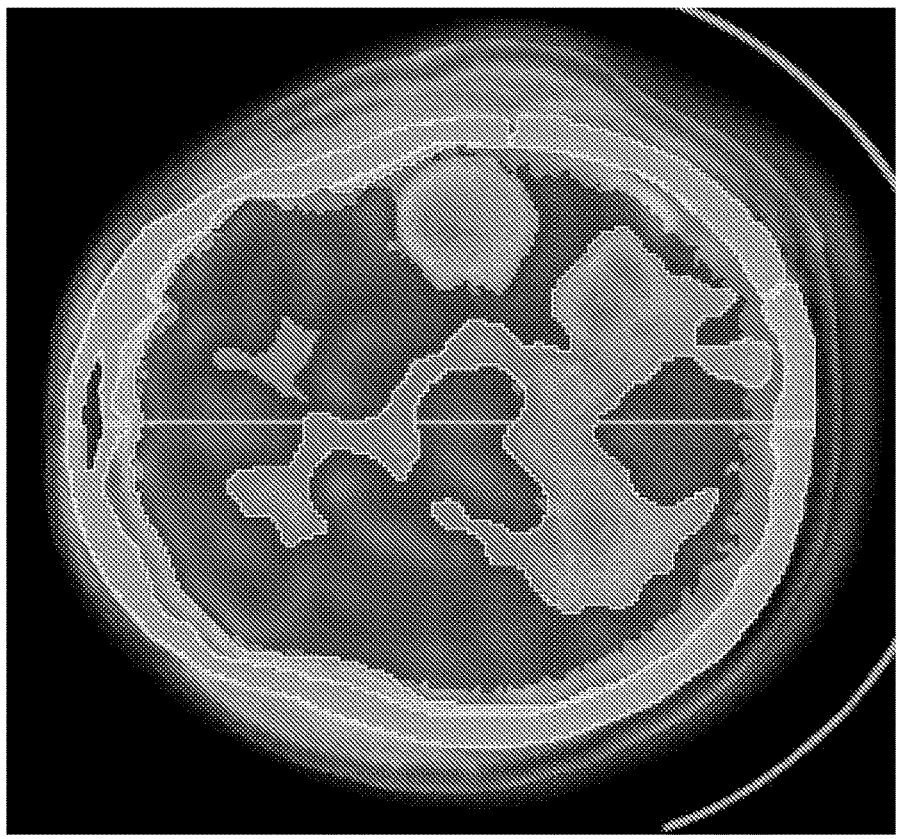
Figure 5A:
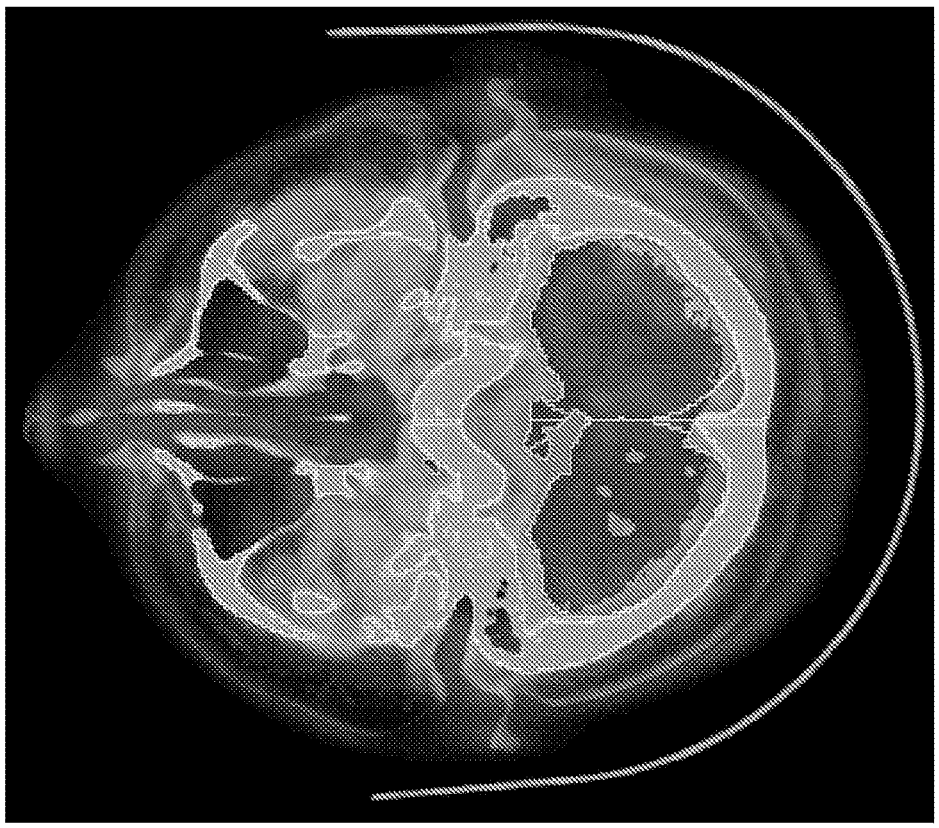
FIGS. 5A and 5B show views somewhat similar to FIGS. 4A and 4B, but in a trans-axial plane through the cerebellum, thus showing segmented areas for the cerebellum and the skull in FIG. 5B, but only for the skull in FIG. 5A.
Figure 5B:
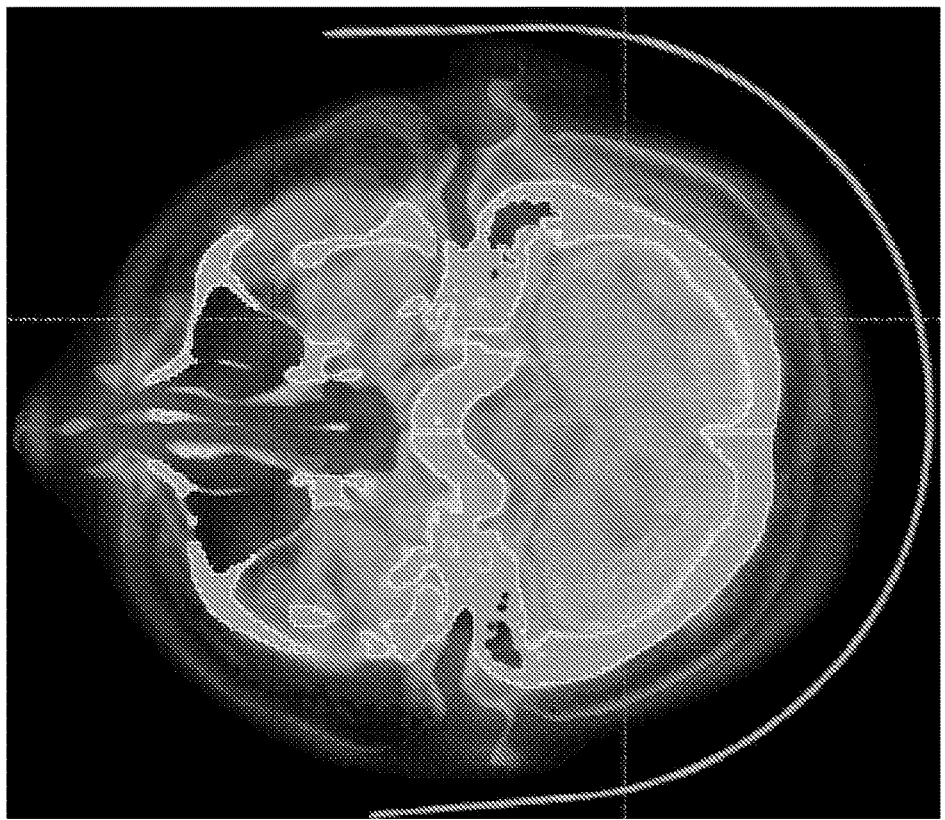
Figure 6A:
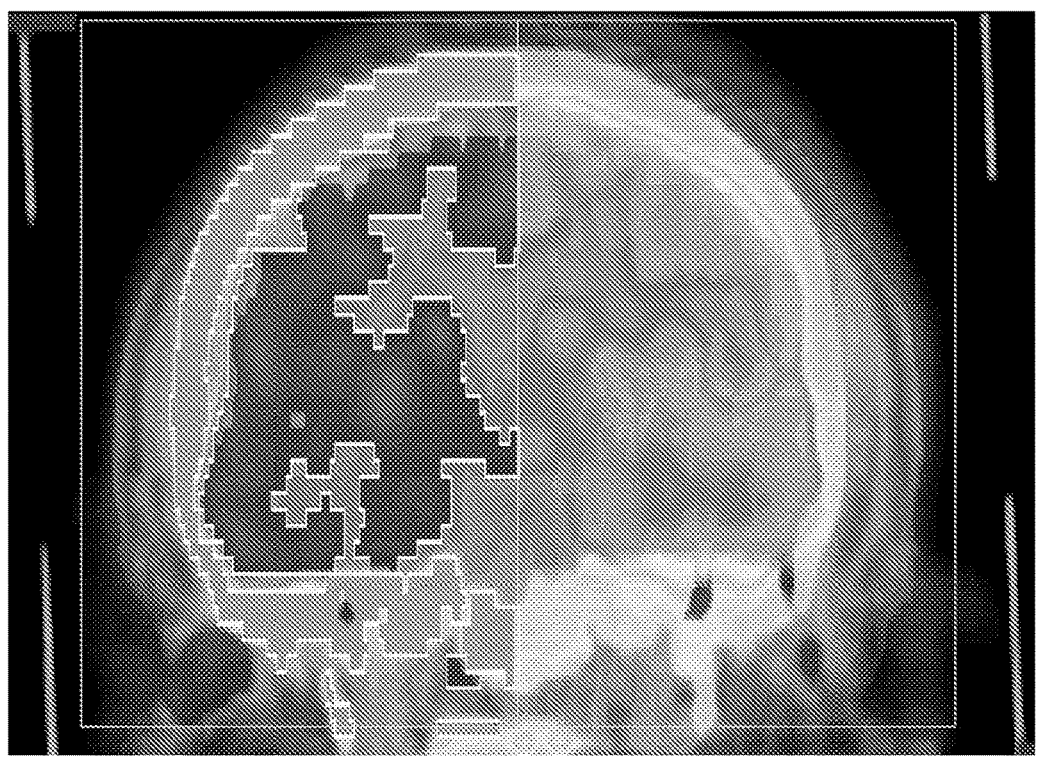
FIG. 6A shows a coronal view of the cerebrum and the skull, with only the left hemisphere being segmented.
Figure 6B:
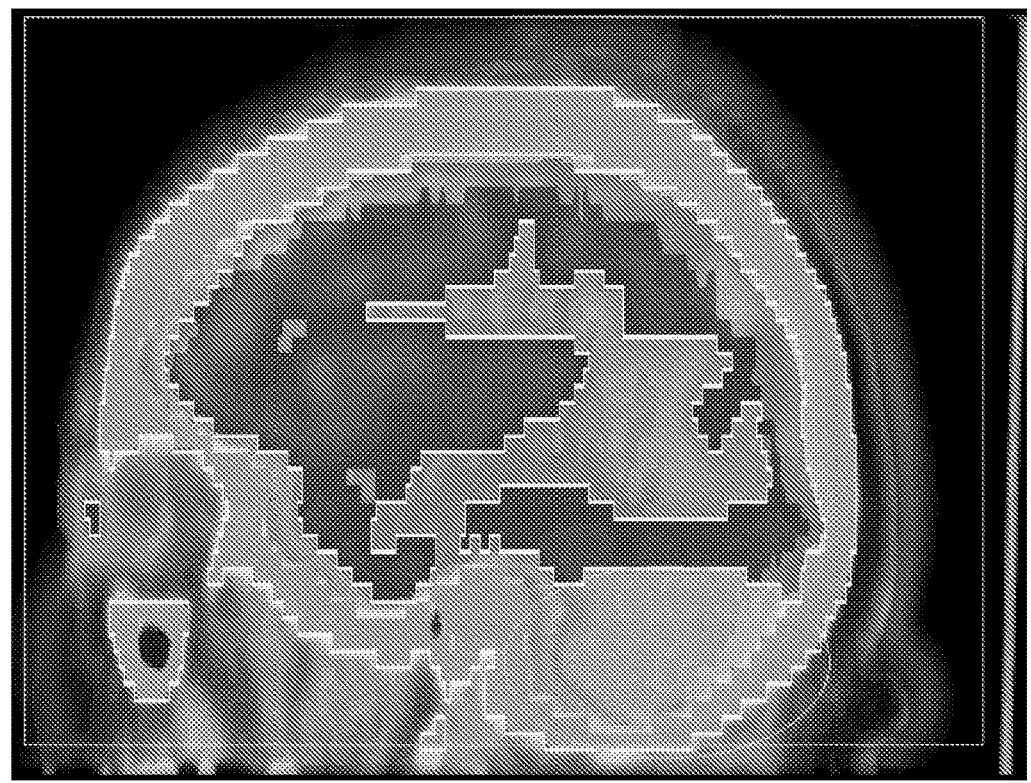
FIG. 6B shows a sagittal view of the skull and the cerebrum and the cerebellum, with segmented regions.

These images illustrate the complexity of performing a subjective analysis based on a perceived normality or abnormality, even when comparing with another image representing a healthy subject. In contrast, the present invention provides an objective, reliable and reproducible output.

EXAMPLES

FDG-PET images of 47 subjects (37 patients and 10 control subjects) were obtained. From these images, total energy metabolism values were calculated. These values are given in tables 1-2.

TABLE 1

Total energy metabolism values after segmentation.

| Subject No. | Diagnosis | Sk_Wh | Sk_L | Sk_R | Br_Wh | Ce_Wh |
|---|---|---|---|---|---|---|
| 1 | NL | 290 | 141 | 149 | 2307 | 2085 |
| 2 | NL | 384 | 195 | 189 | 4256 | 3920 |
| 3 | NL | 383 | 192 | 190 | 3085 | 2809 |
| 4 | NL | 190 | 88 | 102 | 2250 | 2065 |
| 5 | NL | 326 | 164 | 162 | 3515 | 3197 |
| 6 | NL | 378 | 181 | 197 | 6083 | 5665 |
| 7 | NL | 417 | 207 | 210 | 4493 | 4075 |
| 8 | NL | 396 | 205 | 191 | 4570 | 4085 |
| 9 | NL | 347 | 177 | 171 | 3860 | 3497 |
| 10 | NL | 338 | 170 | 168 | 4614 | 4248 |
| 11 | AD | 222 | 114 | 108 | 2496 | 2282 |
| 12 | AD | 196 | 99 | 97 | 3345 | 3062 |
| 13 | AD | 195 | 95 | 100 | 3411 | 3092 |
| 14 | AD | 179 | 86 | 92 | 3369 | 3040 |
| 15 | AD | 148 | 75 | 73 | 2068 | 1877 |
| 16 | AD | 251 | 130 | 121 | 4495 | 4106 |
| 17 | AD | 239 | 117 | 122 | 3019 | 2742 |
| 18 | AD | 184 | 91 | 92 | 2372 | 2149 |
| 19 | AD | 230 | 113 | 117 | 3479 | 3171 |
| 20 | AD | 318 | 159 | 159 | 3836 | 3480 |
| 21 | AD | 186 | 95 | 91 | 3644 | 3334 |
| 22 | AD | 171 | 86 | 86 | 2529 | 2298 |
| 23 | AD | 282 | 139 | 143 | 3274 | 2952 |
| 24 | AD | 296 | 150 | 146 | 1983 | 1763 |
| 25 | AD | 260 | 132 | 129 | 3328 | 3006 |
| 26 | MCI | 189 | 92 | 97 | 2752 | 2481 |
| 27 | MCI | 226 | 119 | 107 | 4375 | 4033 |
| 28 | MCI | 259 | 130 | 129 | 4623 | 4210 |
| 29 | MCI | 299 | 152 | 147 | 2012 | 1797 |
| 30 | MCI | 353 | 173 | 180 | 4464 | 4104 |
| 31 | MCI | 227 | 111 | 116 | 3846 | 3523 |
| 32 | MCI | 212 | 112 | 100 | 3194 | 2969 |
| 33 | MCI | 220 | 112 | 109 | 3505 | 3187 |
| 34 | Glioma | 197 | 101 | 96 | 2595 | 2358 |
| 35 | Glioma | 259 | 130 | 128 | 2436 | 2247 |
| 36 | Glioma | 268 | 131 | 137 | 3079 | 2823 |
| 37 | Glioma | 366 | 181 | 185 | 4091 | 3763 |
| 38 | Glioma | 218 | 109 | 109 | 1853 | 1721 |
| 39 | Glioma | 508 | 240 | 268 | 2878 | 2585 |
| 40 | Glioma | 204 | 103 | 101 | 2254 | 2020 |
| 41 | Glioma | 165 | 86 | 79 | 1981 | 1840 |
| 42 | Glioma | 276 | 130 | 146 | 2844 | 2549 |
| 43 | Glioma | 306 | 155 | 151 | 1993 | 1818 |
| 44 | Glioma | 316 | 160 | 156 | 2681 | 2413 |
| 45 | Glioma | 570 | 295 | 275 | 3952 | 3536 |
| 46 | Glioma | 484 | 229 | 255 | 3013 | 2745 |
| 47 | Glioma | 306 | 156 | 149 | 2522 | 2282 |

Table 1. Total energy metabolism for the brain or skull part in question. Sk_Wh denotes whole skull, Sk_L denotes left hemisphere of skull, Sk_R detotes right hemisphere of skull, Br_Wh denotes whole brain, Ce_Wh denotes whole Cerebrum. NL signifies a control subject. AD signifies a subject diagnosed with Alzheimer's Disease. MCI signifies Mild Cognitive Impairment.

TABLE 2

Total energy metabolism values after segmentation.

| Subject No. | Diagnosis | Ce_L | Ce_R | Cb_Wh | Cb_L | Cb_R |
|---|---|---|---|---|---|---|
| 1 | NL | 1030 | 1055 | 222 | 107 | 115 |
| 2 | NL | 1966 | 1954 | 335 | 157 | 179 |
| 3 | NL | 1443 | 1366 | 276 | 139 | 137 |
| 4 | NL | 901 | 1164 | 185 | 90 | 95 |
| 5 | NL | 1635 | 1562 | 319 | 182 | 137 |
| 6 | NL | 2809 | 2856 | 418 | 219 | 199 |
| 7 | NL | 2013 | 2062 | 419 | 211 | 208 |
| 8 | NL | 2139 | 1947 | 484 | 230 | 254 |
| 9 | NL | 1792 | 1706 | 363 | 180 | 183 |
| 10 | NL | 2155 | 2093 | 366 | 190 | 176 |
| 11 | AD | 1106 | 1176 | 214 | 124 | 90 |
| 12 | AD | 1490 | 1572 | 283 | 138 | 145 |
| 13 | AD | 1471 | 1622 | 318 | 159 | 160 |
| 14 | AD | 1730 | 1310 | 329 | 155 | 174 |
| 15 | AD | 786 | 1091 | 191 | 128 | 62 |
| 16 | AD | 1913 | 2193 | 388 | 211 | 177 |
| 17 | AD | 1477 | 1265 | 277 | 160 | 117 |
| 18 | AD | 943 | 1206 | 224 | 124 | 100 |
| 19 | AD | 1775 | 1397 | 308 | 168 | 140 |
| 20 | AD | 1538 | 1942 | 356 | 201 | 156 |
| 21 | AD | 1668 | 1665 | 311 | 177 | 134 |
| 22 | AD | 1322 | 976 | 231 | 128 | 103 |
| 23 | AD | 1337 | 1615 | 323 | 163 | 160 |
| 24 | AD | 902 | 861 | 220 | 109 | 111 |
| 25 | AD | 1351 | 1655 | 321 | 184 | 137 |
| 26 | MCI | 1324 | 1157 | 271 | 138 | 133 |
| 27 | MCI | 2025 | 2007 | 342 | 166 | 176 |
| 28 | MCI | 2095 | 2115 | 413 | 217 | 196 |
| 29 | MCI | 919 | 879 | 214 | 97 | 118 |
| 30 | MCI | 2034 | 2069 | 360 | 194 | 166 |
| 31 | MCI | 1754 | 1770 | 323 | 152 | 171 |
| 32 | MCI | 1439 | 1530 | 225 | 119 | 105 |
| 33 | MCI | 1631 | 1556 | 319 | 202 | 116 |
| 34 | Glioma | 1100 | 1258 | 237 | 114 | 124 |
| 35 | Glioma | 1225 | 1023 | 189 | 96 | 93 |
| 36 | Glioma | 1328 | 1495 | 256 | 123 | 133 |
| 37 | Glioma | 1524 | 2239 | 328 | 200 | 128 |
| 38 | Glioma | 667 | 1054 | 132 | 84 | 48 |
| 39 | Glioma | 1130 | 1454 | 293 | 152 | 141 |
| 40 | Glioma | 675 | 1344 | 234 | 154 | 80 |
| 41 | Glioma | 1166 | 674 | 141 | 54 | 87 |
| 42 | Glioma | 1525 | 1025 | 294 | 81 | 213 |
| 43 | Glioma | 950 | 868 | 175 | 110 | 66 |
| 44 | Glioma | 1066 | 1347 | 268 | 88 | 181 |
| 45 | Glioma | 1375 | 2161 | 416 | 290 | 126 |
| 46 | Glioma | 1015 | 1731 | 268 | 180 | 87 |
| 47 | Glioma | 1158 | 1124 | 240 | 115 | 125 |

Table 2. Total energy metabolism for the brain or skull part in question. Ce_L denotes left hemisphere of Cerebrum, Ce_R denotes right hemisphere of Cerebrum, Cb_Wh denotes whole Cerebellum, Cb_L denotes left hemisphere of Cerebellum, Cb_R denotes right hemisphere of Cerebellum. NL signifies a control subject. AD signifies a subject diagnosed with Alzheimer's Disease. MCI signifies Mild Cognitive Impairment.

These values may possibly be corrected using comparison of energy metabolism in the left and right hemispheres of the skull.

Further values are calculated based on the measured energy metabolism values or corrected values obtained therefrom. The following equations have been written and standardized so that the results, in normal controls, equal to one.

$$\text{Cerebral Function } (CF) = K_{CF} \frac{Ce_{Wh}}{Br_{Wh}}$$

$$\text{Cerebral Symmetry } I \ (CeSI) = K_{CeSI} \ln \frac{|Ce_L - Ce_R|}{Ce_{Wh}}$$

$$\text{Cerebellar Symmetry } I \ (CbSI) = K_{CbSI} \ln \frac{|Cb_L - Cb_R|}{Cb_{Wh}}$$

$$\text{Cerebral Symmetry } II \ (CeSII) = K_{CeSII} \frac{\text{Min}(Ce_L, Ce_R)}{\text{Max}(Ce_L, Ce_R)}$$

$$\text{Cerebellar Symmetry } II \ (CbSII) = K_{CbSII} \frac{\text{Min}(Cb_L, Cb_R)}{\text{Max}(Cb_L, Cb_R)}$$

$$\text{Skull-cerebellar ratio } (SVI) = K_{SVI} \frac{Sk_{Wh}}{Cb_{Wh}}$$

$$\text{Skull-cerebral ratio } (SVII) = K_{SVII} \frac{Sk_{Wh}}{Ce_{Wh}}$$

Here, Min(X, Y) is the minimum value of X and Y, and Max(X, Y) is the maximum value of X and Y.

Constants (K) in each equation are as follows:

$$K_{CeSI} = K_{CbSI} = -0.33$$

$$K_{CeSII} = 1.08$$

$K_{CbSII} = K_{SVI} = 1.11$ $K_{CF} = 1.12$ $K_{SVII} = 10$

These above constants are set to give unity values (i.e. values of 1) for healthy control subjects.

The above defined values (CF, CeS I, CbS I, CeS II, CbS II, SV I, SV II) are calculated to see if a value below or above 1 was obtained. Simplified values TCF, TCeS I, TCbS I, TCeS II, TCbS II, TSV I, and TSV II were then obtained as 1 (binary true) when the corresponding equation gave a result above 1, and 0 (binary false) when the corresponding equation gave a result not above 1.

Then, a brain function score was defined as follows:

$$BFS = 4CF + 4\text{Max}(CeSI, CbSI) + 4\text{Max}(CeSII, SVI) + \text{Max}(CbSII, SVII) - 3$$

The obtained values are listed in table 3.

TABLE 3

Brain function score (BFS) for subjects 1-47 are listed.

| No. | Diagnosis | BFS |
|---|---|---|
| 1 | NL | 10 |
| 2 | NL | 9 |
| 3 | NL | 10 |
| 4 | NL | 10 |
| 5 | NL | 10 |
| 6 | NL | 9 |
| 7 | NL | 10 |
| 8 | NL | 9 |
| 9 | NL | 10 |
| 10 | NL | 10 |
| 11 | AD | 5 |
| 12 | AD | 6 |
| 13 | AD | 6 |
| 14 | AD | 6 |
| 15 | AD | 1 |
| 16 | AD | 1 |
| 17 | AD | 1 |
| 18 | AD | 1 |
| 19 | AD | 1 |
| 20 | AD | 1 |
| 21 | AD | 5 |
| 22 | AD | 1 |
| 23 | AD | 6 |
| 24 | AD | 6 |
| 25 | AD | 1 |
| 26 | MCI | 6 |
| 27 | MCI | 5 |
| 28 | MCI | 10 |
| 29 | MCI | 10 |
| 30 | MCI | 9 |
| 31 | MCI | 10 |
| 32 | MCI | 10 |
| 33 | MCI | 9 |
| 34 | Glioma | 1 |
| 35 | Glioma | 10 |
| 36 | Glioma | 10 |
| 37 | Glioma | 5 |
| 38 | Glioma | 6 |
| 39 | Glioma | 6 |
| 40 | Glioma | 2 |
| 41 | Glioma | 5 |
| 42 | Glioma | 6 |
| 43 | Glioma | 10 |
| 44 | Glioma | 6 |
| 45 | Glioma | 6 |
| 46 | Glioma | 6 |
| 47 | Glioma | 10 |

Theoretically, the above function may give values between −3 and 10; however, in a living brain, all the numbers in Table 3 can hardly equal to zero. For example, a clinically impaired brain should the value of about 1, whereas a clinically healthy brain gets the maximum values. Minus numbers are left for brain death, comatose state, severe encephalopathies, or very severely impaired brain conditions.

Table 3 shows BFS values for each patient. One may easily distinguish the difference between disease groups. Results show the status of the brain with only one number which makes it easy to understand how good the patient's condition is.

A more advanced approach is obtained by using the following equation:

$$\psi_n = (K_{i_n} CeF)^{\lambda.in}(K_{ii_n} 20^{CeSI})^{\lambda.iin}(K_{iii_n} 20^{CbSI})^{\lambda.iiin}(K_{iv_n} CeSII)^{\lambda.ivn}(K_{v_n} CbSII)^{\lambda.vn}(K_{vi_n} SVI)^{\lambda.vin}(K_{vii_n} SVII)^{\lambda.viin}$$

For the purpose of this example, the above equation is executed as $\psi_1$-$\psi_6$ and $\psi_{ext}$, using the constants defined in table 4.

TABLE 4

| | Constants | | | | | | | |
|---|---|---|---|---|---|---|---|---|
| Constants | | $\psi_1$ | $\psi_2$ | $\psi_3$ | $\psi_4$ | $\psi_5$ | $\psi_6$ | $\psi_{ext}$ |
| Coefficients | $K_i$ | 1 | 1 | 1 | 1 | 1 | 1 | 1 |
| | $K_{ii}$ | 2 | 2 | 2 | 2 | 2 | 2 | 2 |
| | $K_{iii}$ | 2 | 2 | 2 | 2 | 2 | 2 | 2 |
| | $K_{iv}$ | 0.96 | 0.96 | 0.96 | 0.96 | 0.96 | 0.96 | 0.96 |
| | $K_v$ | 1 | 1 | 1 | 1 | 1 | 1 | 1 |
| | $K_{vi}$ | 0.9 | 0.9 | 0.9 | 0.9 | 0.9 | 0.9 | 0.9 |
| | $K_{vii}$ | 1 | 1 | 1 | 1 | 1 | 1 | 1 |
| Expo | $\lambda_i$ | 3500 | 3500 | −800 | −800 | 0 | −5000 | 0 |
| | $\lambda_{ii}$ | 10 | 5 | 0 | 26 | 0 | 20 | 190 |
| | $\lambda_{iii}$ | 0 | 8 | 40 | −25 | 0 | −350 | −500 |
| | $\lambda_{iv}$ | 1500 | 1500 | 1500 | 1500 | 0 | 0 | 0 |
| | $\lambda_v$ | 100 | 100 | 200 | 200 | 4000 | −200 | 0 |
| | $\lambda_{vi}$ | −150 | 200 | 0 | 0 | 15000 | 1400 | 0 |
| | $\lambda_{vii}$ | −100 | 200 | −600 | −10 | 15000 | 1000 | 0 |

Table 4. Constants including coefficients and exponents for use in calculation of $\psi_n$.

It is noted that the above constants listed in table 4, i.e. $K_{i_n\text{-}vii_n}$, and $\lambda_{i_n\text{-}vii_n}$, are constants in $n^{th}$ equation. A set of equations may be written in this form with altered constants differentiating various diseases.

Using this, $\psi_1$-$\psi_6$ and $\Omega_{ext}$ are calculated. Typically, either very high numbers above 100000 or numbers very close to zero are obtained. For the purpose of the present example, a threshold value of 100000 is used to signify "large numbers", whereas numbers below 10000 signify a "small number". Intermediate numbers signify uncertainty with respect to the result, whereas extreme numbers (very high, very low) signify a higher degree of certainty.

Finally, the below list of questions was used to determine an indication of the diagnosis:

1) Is $\psi_6$ a large number? If yes, the brain status indication parameter indicates glioma.
2) If question 1) is no, is $\psi_5$ a large number, and is $\psi_{ext}$ a small number? If yes, the brain status indication parameter indicates glioma.
3) If question 2) is no, are all of $\psi_1$, $\psi_2$, and $\psi_3$ large numbers? If yes, the brain status indication parameter indicates normal condition.
4) If question 3) is no, is $\psi_4$ a small number and $\psi_5$ a large number? If yes, the brain status indication parameter indicates glioma.
5) If question 4) is no, is at least five of $\psi_1$, $\psi_2$, $\psi_3$, $\psi_4$, $\psi_5$, $\psi_6$, and $\psi_{ext}$ large numbers? If yes, the brain status indication parameter indicates glioma.
6) If question 5) is no, is $\psi_{ext}$ a large number, and is BFS at least 8? If yes, the brain status indication parameter indicates MCI.
7) If question 6) is no, the brain status indication parameter indicates Alzheimer's disease.

Evaluating the above described method, the following results were obtained:

First, it was evaluated how accurate the above described method was when differentiating diseased from healthy, the results are indicated in table 5.

TABLE 5

Here, "Test +" indicates a positive result for a brain condition from the brain status indication parameter, "Test −" indicates a negative result, "Disease +" indicates subject having a brain disorder, and "Disease −" indicates subject within brain disorder.

|  | Disease + | Disease − | Totals |
|---|---|---|---|
| Test + | 36 | 0 | 36 |
| Test − | 1 | 10 | 11 |
| Totals | 37 | 10 | 47 |

As can be seen from table 5, only 1 out of 47 was wrongly indicated to have a disease by the brain status indication parameter.

When differentiating Alzheimer's disease (AD) from MCI, the results are indicated in table 6.

TABLE 6

"AD" indicates subjects with AD.
"MCI" indicates subjects with MCI.

|  | AD | MCI | Totals |
|---|---|---|---|
| Predicted AD | 15 | 2 | 17 |
| Predicted MCI | 0 | 5 | 5 |
| Totals | 15 | 7 | 22 |

From table 6, the following was concluded:
Sensitivity=100%
Specificity=71.4%
Positive predictive values (PPV)=88.2%
Negative predictive values (NPV)=100%
Accuracy=90.9%

When differentiating AD from Glioma, the results are indicated in table 7.

TABLE 7

|  | AD | Glioma | Totals |
|---|---|---|---|
| Predicted AD | 15 | 1 | 16 |
| Predicted Glioma | 0 | 13 | 13 |
| Totals | 15 | 14 | 29 |

From table 7, the following was concluded:
Sensitivity=100%
Specificity=92.8%
PPV=93.7%
NPV=100%
Accuracy=96.5%

When differentiating Glioma from MCI, the results are indicated in table 8.

TABLE 8

|  | Glioma | MCI | Totals |
|---|---|---|---|
| Predicted Glioma | 13 | 0 | 13 |
| Predicted MCI | 0 | 5 | 5 |
| Totals | 13 | 5 | 18 |

From table 8, the following was concluded:
Sensitivity=100%
Specificity=100%
PPV=100%
NPV=100%
Accuracy=100%

A total summation of results with respect to accuracy are indicated in table 9.

TABLE 9

|  |  | Disease | | | | |
|---|---|---|---|---|---|---|
|  |  | NL | AD | MCI | Glioma | Totals |
| Predicted | NL | 10 | 0 | 1 | 0 | 11 |
|  | AD | 0 | 15 | 2 | 1 | 18 |
|  | MCI | 0 | 0 | 5 | 0 | 5 |
|  | Glioma | 0 | 0 | 0 | 13 | 13 |
|  | Totals | 10 | 15 | 8 | 14 | 47 |

"NL" indicates a control subject without a brain disorder.

As can be seen from table 9, the overall accuracy obtained was 91.48%.

Therefore, it was concluded that the presently described the brain status indication parameter according to the present invention results in a very accurate indication of brain disorders, both with respect to the presence of a brain disorder and with respect to the specific brain disorder.

FIGURE REFERENCES

BR. Brain
SK. Skull

LCE. Left hemisphere of cerebrum
RCE. Right hemisphere of cerebrum
LCB. Left hemisphere of cerebellum
RCB. Right hemisphere of cerebellum
BSI. Brain status indication parameter
BEM. Brain energy metabolism indicator
SEM. Skull energy metabolism indicator
SEG. Segmentation step
DBI. Determining brain energy metabolism indicator step
DSI. Determining skull energy metabolism indicator step
EBI. Establish brain status indication parameter
MES. Measuring step
DFP. Demining further parameter(s) step
EDI. Establish diagnosis step
TRT. Treatment step
BSD. Brain scanning device
SUB. Subject
CD. Computer device
BSS. Brain status establishment system

The invention claimed is:

1. A method of establishing a brain status indication parameter indicative of a brain disorder, comprising:
   recording a brain glucose metabolism image of at least a part of a brain of a subject by a neuroimaging brain scanning device;
   recording a skull glucose metabolism image of at least a part of a skull of said subject by said neuroimaging brain scanning device;
   determining, by a computer device and from the brain glucose metabolism image, a brain glucose metabolism indicator, the brain glucose metabolism indicator being a first value associated brain glucose metabolism;
   determining, by the computer device and from the skull glucose metabolism image, a skull glucose metabolism indicator, the skull glucose metabolism indicator being a second value associated with skull glucose metabolism; and
   determining, by the computer device, the brain status indication parameter by at least calculating a ratio between the brain glucose metabolism indicator and the skull glucose metabolism indicator, or vice versa.

2. The method according to claim 1, wherein the method further comprises establishing a degree of symmetry between at least a part of a right cerebral or cerebellar hemisphere of the brain and a corresponding part of a left cerebral or cerebellar hemisphere of the brain.

3. The method according to claim 2, wherein the degree of symmetry comprises a ratio between at least a part of the right cerebral or cerebellar hemisphere of the brain and a corresponding part of the left cerebral or cerebellar hemisphere of the brain.

4. The method according to claim 1, wherein the brain glucose metabolism image comprises a brain glucose metabolism indicator distribution and the skull glucose metabolism image comprise a skull glucose metabolism indicator distribution; and
   wherein said brain glucose metabolism indicator is determined from a brain glucose metabolism indicator distribution and wherein said skull glucose metabolism indicator is determined from the skull glucose metabolism indicator distribution.

5. The method according to claim 1, wherein the brain glucose metabolism image comprises a brain glucose metabolism indicator distribution; and
   wherein determining the brain glucose metabolism indicator comprises segmenting on the brain glucose metabolism indicator distribution is performed to obtain the brain glucose metabolism indicator.

6. The method according to claim 1, wherein the method further comprises determining one or more further brain glucose metabolism indicators of at least a part of the brain of the subject and of at least a part of the skull of the subject.

7. The method according to claim 1, wherein the method further comprises determining one or more further skull glucose metabolism indicators of at least a part of the skull of the subject.

8. The method according to claim 5, wherein the method further comprises segmenting the brain glucose metabolism indicator distribution into a number of regularly shaped three-dimensional zones.

9. The method according to claim 8, wherein the method further comprises determining a synaptic entropy network indication parameter by recording a number of brain glucose metabolism images to form a three-dimensional representation of the brain and, for each image, calculating a partial synaptic entropy indicator as $$H_S = - \sum_{\substack{1 \leq i \leq m \\ 1 \leq j \leq n}} P_{i,j} \log_b P_{i,j}$$

where i and j represent a location of each pixel of the image, m is a number of rows, n is a number of columns, and b is a base of logarithm,
where a synaptic entropy indicator is calculated as $$H_T = \Sigma H_S$$

where the synaptic entropy network indication parameter is calculated by at least relating said synaptic entropy indicator to a corresponding normalized synaptic entropy indicator, where the normalized synaptic entropy indicator is calculated as an average synaptic entropy network indication parameter for at least 30 healthy subjects.

10. The method according to claim 1, wherein the brain glucose metabolism image is recorded using a neuroimaging technique selected from a group consisting of a functional Magnetic Resonance Imaging (fMRI) based technique, a Computed Tomography (CT) Scan based technique, a Positron Emission Tomography (PET) based technique, a Magnetoencephalography (MEG) or Electroencephalography (EEG) based technique, a Single-photon emission computed tomography (SPECT) based technique, or an ultrasound-based technique.

11. The method according to claim 1, wherein the brain status indication parameter gives an indication of a presence of the brain disorder or not.

12. The method according to claim 1, wherein the brain status indication parameter gives an indication of a type of the brain disorder.

13. The method according to claim 1, wherein the brain disorder is selected from a group consisting of diaschisis; brain tumor; Mild Cognitive Impairment (MCI); and Alzheimer's disease (AD).

14. The method according to claim 1, wherein the brain status indication parameter is indicative of a ratio of a glucose metabolism indicator of a cerebrum of the brain to the brain as a whole and a relation between said brain glucose metabolism indicator to said skull glucose metabolism indicator.

15. A brain status establishment system for establishing a brain status indication parameter indicative of a brain disorder, the system comprising:
- a neuroimaging brain scanning device configured to
  - record a brain glucose metabolism image of at least a part of a brain of a subject; and
  - record a skull glucose metabolism image of at least a part of a skull of the subject; and
- a computer device comprising instructions which, when executed by the computer device, causes the computer device to perform operations comprising:
  - determining, from the brain glucose metabolism image, a brain glucose metabolism indicator, the brain glucose metabolism indicator being a first value associated brain glucose metabolism;
  - determining, from the skull glucose metabolism image, a skull glucose metabolism indicator, the skull glucose metabolism indicator being a second value associated with skull glucose metabolism; and
  - determining the brain status indication parameter by at least calculating a ratio between the brain glucose metabolism indicator and skull glucose metabolism indicator, or vice versa.

16. A method of treating a disease comprising:
establishing a brain status indication parameter indicative of a brain disorder by:
- recording a brain glucose metabolism image of at least a part of a brain of a patient by a neuroimaging brain scanning device;
- recording a skull glucose metabolism image of at least a part of a skull of the patient by the neuroimaging brain scanning device;
- determining, by a computer device and from the brain glucose metabolism image, a brain glucose metabolism indicator, the brain glucose metabolism indicator being a first value associated with brain glucose metabolism;
- determining, by the computer device and from the skull glucose metabolism image, a skull glucose metabolism indicator, the skull glucose metabolism indicator being a second value associated with skull glucose metabolism; and
- determining, by the computer device, the brain status indication parameter by at least calculating a ratio between the brain glucose metabolism indicator and the skull glucose metabolism indicator, or vice versa; and treating the patient, wherein the treating comprises administering a drugs, performing surgery, and/or performing physical exercise.

17. A method of treating a disease comprising performing the method according to claim 1 before performing physical exercise.

* * * * *